United States Patent [19]

Ichinohe et al.

[11] Patent Number: 4,981,988
[45] Date of Patent: Jan. 1, 1991

[54] ORGANOSILOXANE COMPOUND WITH ONE END STOPPED WITH AN AMINOALKYL GROUP AND A MANUFACTURING METHOD THEREOF

[75] Inventors: Shoji Ichinohe; Yoshitaka Hamada, both of Annaka, Japan

[73] Assignee: Shin-Etsu Chemical Co., Ltd., Tokyo, Japan

[21] Appl. No.: 303,176

[22] Filed: Jan. 30, 1989

[30] Foreign Application Priority Data

Jan. 29, 1988 [JP] Japan ................... 63-18602

[51] Int. Cl.$^5$ .............................. C07F 7/10
[52] U.S. Cl. ................................. 556/425
[58] Field of Search ........................ 556/425

[56] References Cited

U.S. PATENT DOCUMENTS

| | | | |
|---|---|---|---|
| 2,966,507 | 12/1960 | Montgomery | 556/425 X |
| 3,033,815 | 5/1962 | Pike et al. | 556/425 X |
| 3,044,982 | 7/1962 | Jex et al. | 556/425 X |
| 3,087,909 | 4/1963 | Morehouse et al. | 556/425 X |
| 4,152,346 | 5/1979 | Seiler et al. | 556/425 X |
| 4,645,614 | 2/1987 | Goossens et al. | 556/425 X |

FOREIGN PATENT DOCUMENTS 2185984 8/1987 United Kingdom ............ 556/425

Primary Examiner—Paul F. Shaver
Attorney, Agent, or Firm—Millen, White & Zelano

[57] ABSTRACT

A novel organosiloxane compound of the formula

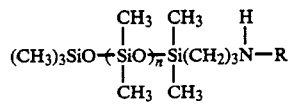

wherein R is either hydrogen atom or an alkyl having 1-3 carbon atoms, and n is an integer such that $0 \leq n \leq 1,000$, is effective in improving surface characteristics of synthetic silicon resins in which it is contained such as oxygen permeability and surface slip factor, and is produced by reacting a cyclic silazane of the formula

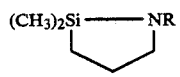

with a silanol of the formula

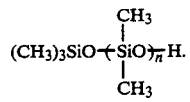

7 Claims, No Drawings

ORGANOSILOXANE COMPOUND WITH ONE END STOPPED WITH AN AMINOALKYL GROUP AND A MANUFACTURING METHOD THEREOF

BACKGROUND OF THE INVENTION

The present invention relates to a novel organosiloxane compound one of whose ends is stopped with an aminoalkyl group and a method of manufacturing such a compound.

An organosiloxane compound with both ends stopped with aminoalkyl is known. There are various examples of such a compound, and one of them is represented by the following formula wherein both ends are stopped with an aminopropyl group:

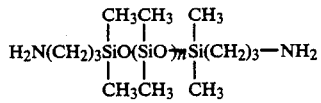

These organosiloxanes with both ends stopped with aminoalkyl are used to obtain modified siloxane compounds. The modification of the organosiloxanes lies in reactions between the amino groups of the organosiloxanes and the "acid anhydride group" [—CO—O—CO— in (RCO)$_2$O], carboxyl group, isocyanato group, epoxy group, etc. of other monomer compounds. The thus modified siloxane compounds are effective, when included in the raw materials for syntheses of a polyimide resin, a polyamide resin, or a polyurea resin, in imparting to these resins high oxygen permeability, high surface slip factor, and other desirous surface characteristics which are inherent in silicone resins.

However, the surface improving effects caused by the inclusion of a siloxane both of whose ends are stopped with aminoalkyl are not satisfactory. Further improvements, especially in oxygen permeability and surface slip factor in the resulting synthetic resins are desired. It is believed that the existence of the relatively reactive amino group at each end of the siloxane chain leads to a reaction that causes the siloxane chain to have no free end, whereby the surface improving effects of the siloxane are spoiled.

Furthermore, when reacted with a polyfunctional monomer which has in it three or more functional groups such as an acid anhydride group, carboxyl group, isocyanato group, and epoxy group, an organic siloxane with both ends stopped with aminoalkyl undergoes gelatinization to thereby lose its surface improving effects.

It was speculated that the use of an organosiloxane with only one end stopped with an aminoalkyl group would solve these problems. However, neither such organosiloxane nor a method of manufacturing the same was known.

OBJECT OF THE INVENTION

It is, therefore, the primary object of the invention to provide an organosiloxane compound only one of whose ends is stopped with an aminoalkyl group and a method of manufacturing such a compound.

It is another object of the invention to provide an organosiloxane compound which is effective to improve surface characteristics of synthetic resins produced therefrom such as oxygen permeability and surface slip factor, and a method of manufacturing such a compound.

The foregoing and other objects, features and advantages of the present invention will be apparent from the following detailed description thereof.

SUMMARY OF THE INVENTION

The foregoing objects are attained by an organosiloxane compound one of whose ends is stopped with an aminoalkyl group generally represented by Formula (I):

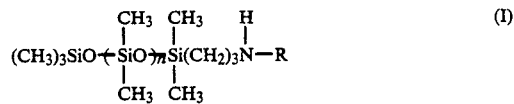

wherein R is either hydrogen atom or an alkyl having 1-3 carbon atoms, and n is an integer such that $0 \leq n \leq 1,000$.

In practice, however, the organosiloxane compound of Formula (I) is always prepared in the form of a mixture of numerous molecules of Formula (I) differing in the number n depending on the degree of polymerization, and therefore the actual requirement is that the mean value of n is 0, 1,000 or any whole or fractional number therebetween.

The organosiloxane compound (I) is obtained, for example, by reacting a cyclic silazane represented by Formula (II) wherein R is the same as that in (I):

with a silanol or a mixture of silanols represented by Formula (III):

wherein the integer n is equal to that in (I).

DETAILED DISCLOSURE

Of the compounds of Formula I, those wherein R is methyl, and those wherein n is an integer from 0 to 500 are preferred.

The cyclic silazane (II) is obtained, for example, by means of the method described in U.S. Pat. No. 3,146,250, whose disclosure is incorporated herein by reference, that is, by reacting a compound of the formula

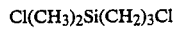

with ammonia or an alkyl amine, preferably of 1 to 3 carbon atoms, i.e., methyl amine, ethyl amine and propyl amine.

The reaction between the cyclic silazane (II) and the silanol (III) is normally conducted in the absence of a solvent, or, depending on the requirements, in an aprotic organic solvent, such as (i) an aromatic hydrocarbons solvent, e.g. benzene, toluene, xylene, (ii) an aliphatic hydrocarbons solvent, e.g. octane, (iii) a chlorinated hydrocarbons solvent, e.g. carbon tetrachloride, trichloroethane, (iv) a ketone, e.g. methyl ethyl ketone, methyl isobutyl ketone, (v) an ether, e.g. tetrahydrofuran, butyl ether, and (vi) an ester, e.g. ethyl acetate, butyl acetate. Although the reaction can be conducted at a temperature between 0° and 200° C., it preferably is conducted at a temperature between 0° and 120° C.

The relative proportions of the cyclic silazane (II) and the silanol (III) in the reaction mixture are determined based on the desired organosiloxane compound with one end stopped with an aminoalkyl group (I). Preferably, the amount of the cyclic silazane (II) employed is 5 to 20 mol. % greater than its stoichiometrically equivalent value with respect to the silanol (III), and when the reaction is completed, the unreacted cyclic silazane is removed by distillation.

EXAMPLES

In the following description of the examples, the method of the present invention is more clearly explained.

EXAMPLE 1

Synthesis of N-methyl-γ-aminopropylpentamethyldisiloxane:

9.0 g. (0.1 mol) of trimethylsilanol and 12.9 g. (0.1 mol) of the cyclic silazane compound represented by Formula (IV) were mixed together in a flask at room temperature. An exothermic reaction immediately occurred.

After the reaction continued for thirty minutes, the reaction mixture was distilled at 200° to 202° C. A colorless transparent liquid weighing 17 g. was obtained as the distillate. The yield of the liquid was 78%. The H-NMR spectrum, IR spectrum, and mass spectrum of the liquid were observed. The results were:

$^1$H-NMR (δ, CCl$_4$, ppm): 2.50 (N—CH$_2$—C, t, 2H), 2.35 (N—CH$_3$, s, 3H), 1.77-1.17 (C—CH$_2$—C and N—H, m, 3H), 0.77-0.32 (C—CH$_2$—Si, m, 2H), 0.08 (SiCH$_3$, s, 15H).

IR(KBr, cm$^{-1}$): 3290 (N—H), 1254 (Si—CH$_3$), 1061 (Si—O) mass m/e: 219 (M+)

According to these data, the transparent, liquid was a siloxane compound represented by Formula (V):

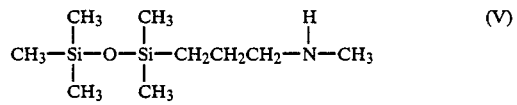

EXAMPLE 2

Synthesis of dimethylsiloxane having one end stopped with N-methyl-γ-aminopropyl:

(1) A dimethylsiloxane oligomer of a mean molecular weight of 2220 represented by Formula (VI) was obtained by the reaction of 9 g. (0.1 mol) of trimethylsilanol with 207.2 g. of hexamethylcyclotrisiloxane, in the presence of 25 mg. of a catalyst having Formula (VII) and 8 g. of acetonitrile:

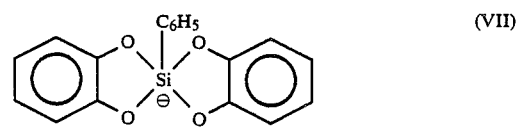

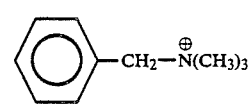

(2) The dimethylsiloxane oligomer obtained in step (1) in an amount of 216.2 g. was heated to and kept at a temperature of 80° C., while 15.5 g. (0.12 mol) of the same cyclic silazane used in Example 1 was dripped into the dimethylsiloxane oligomer. From the start of the dripping the reaction was continued for two hours. Then, the volatile components were removed by distillation under a reduced pressure of 3 mm Hg and at a temperature of 130° C., leaving 208 g. of colorless transparent liquid as the residual liquid. The results of the IR spectrum, a quantitative analysis of amino group, and the gel permeation chromatographic analysis were as follows:

IR(KBr, cm$^{-1}$): 3400 (N—H), 1261 (Si—CH$_3$), 1094, 1024 (Si—O) amine equivalence (molecular weight per one amino group): 2136 (theoretically 2291)

GPC:

The number average molecular weight (Mn) was 2900 on the supposition that the liquid substance were a polystyrene.

The weight average molecular weight (Mw) was 3600 on the supposition that the liquid substance were a polystyrene.

The degree of polydispersion (Mw/Mn) was 1.24.

It follows from these data that the formula of the liquid substance is as follows:

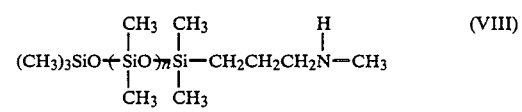

wherein n is about 28.

The siloxane compound of Example 1 represented by Formula (V), and the siloxane compound of Example 2 represented by Formula (VIII) are novel in that each has only one end stopped with an aminoalkyl group. This kind of siloxane compound is effective in improving the surface qualities of various resins when it is added therein during the manufacturing process. Since the siloxanes obtained in Examples 1 and 2 have N-methylaminopropyl at only one end, the other end of each remains free even if these siloxanes are reacted with monomer compounds carrying other kinds of functional groups such as carboxyl, isocyanate and epoxy, in a synthesis of a resin; wherefore the resulting modified silicone resin has far improved surface characteristics such as slip factor compared with a conventional silicone resin based on a corresponding siloxane having an amino group at both its ends.

Also, because the siloxane compound of the invention cannot participate in the polymerization, and, being monofunctional, does not gelatinize even when attacked by a trifunctional monomer or more functional ones, one can obtain desirably modified siloxane resins.

Furthermore, since the structure of siloxane compounds of this invention is such that they exhibit polarity, they can be employed as surface active agents as well as emulsifying agents and auxiliary emulsifying agents. The surface activation effect is improved when the siloxane compound is in acid addition salt form, viz., a salt of an organic or inorganic acid, e.g., an acetate, a hydrochloride, or an ammonium salt which are obtained by reacting the amino group in the aminoalkyl with acetic acid, hydrochloric acid, or an alkyl halide, respectively.

Contemplated equivalents of the compounds of this invention are those otherwise corresponding thereto wherein one, and/or one or both of methyl groups on the bridging silicon atom or atoms is another non-interfering aliphatic or aryl group, e.g., ethyl or phenyl.

While this invention has been described in terms of specific embodiments thereof, other forms may be readily adapted by one skilled in the art. Accordingly, the scope of the invention is to be limited only by the claims following.

What is claimed is:

1. A method for producing an organosiloxane compound of the formula:

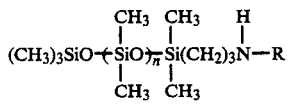

comprising the step of reacting a cyclic silazane of the formula:

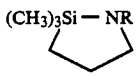

with a silanol of the formula:

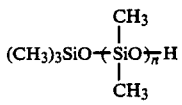

wherein in each instance R is either a hydrogen atom or alkyl of 1-3 carbon atoms and n is an integer such that $0 \leq n \leq 1,000$.

2. A method of claim 1 wherein R is methyl.

3. A method of claim 1 wherein the reaction between the cyclic silazane and the silanol is conducted in the absence of a solvent.

4. A method of claim 1 wherein the reaction between the cyclic silazane and the silanol is conducted in an aprotic organic solvent.

5. A method of claim 1 wherein the reaction between the cyclic silazane and the silanol is conducted at an elevated temperature of up to 120° C.

6. A method of claim 1 wherein a 5 to 20 mol. % excess of the cyclic silazane is employed and when the reaction is complete the unreacted cyclic silazane is removed by distillation.

7. A method of claim 6 wherein R is methyl and the reaction between the cyclic silazane and the silanol is conducted at an elevated temperature of up to 120° C.

* * * * *